(12) United States Patent
Mielenz

(10) Patent No.: US 9,249,442 B2
(45) Date of Patent: Feb. 2, 2016

(54) CONSOLIDATED BIOPROCESSING METHOD USING THERMOPHILIC MICROORGANISMS

(71) Applicant: UT-Battelle, LLC, Oak Ridge, TN (US)

(72) Inventor: Jonathan Richard Mielenz, Rockwood, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 183 days.

(21) Appl. No.: 13/762,619

(22) Filed: Feb. 8, 2013

(65) Prior Publication Data

US 2013/0210071 A1    Aug. 15, 2013

Related U.S. Application Data

(60) Provisional application No. 61/596,962, filed on Feb. 9, 2012.

(51) Int. Cl.
| | | |
|---|---|---|
| *C12N 1/20* | (2006.01) | |
| *C12P 39/00* | (2006.01) | |
| *C12P 7/10* | (2006.01) | |
| *C12P 7/14* | (2006.01) | |
| *C12P 7/54* | (2006.01) | |

(52) U.S. Cl.
CPC . *C12P 39/00* (2013.01); *C12N 1/20* (2013.01); *C12P 7/10* (2013.01); *C12P 7/14* (2013.01); *C12P 7/54* (2013.01); *C12P 2203/00* (2013.01); *Y02E 50/16* (2013.01)

(58) Field of Classification Search
None
See application file for complete search history.

(56) References Cited

U.S. PATENT DOCUMENTS

| | | | |
|---|---|---|---|
| 8,327,823 B2 * | 12/2012 | Courtoy et al. | ............... 123/299 |
| 2010/0120106 A1 | 5/2010 | Kohn et al. | |
| 2010/0137647 A1 | 6/2010 | Bradin | |
| 2010/0159553 A1 | 6/2010 | Bradin | |
| 2010/0304420 A1 | 12/2010 | Gray | |

FOREIGN PATENT DOCUMENTS

| | | |
|---|---|---|
| CN | 101591679 A | 12/2009 |
| WO | 2008100251 | 8/2008 |

OTHER PUBLICATIONS

Weimer et al., 1977. Fermentation of Cellulose and Cellobiose by Clostridium thermocellum in the Absence and Presence of Methanobacterium thermoautotrophicum. Applied and Environmental Microbiology, vol. 33, No. 2, pp. 289-297.*
Boggan 2003. Alcohol, Chemistry and You. http://www.chemcases.com/alcohol/alc-03.htm. Downloaded May 17, 2010). Sources and Uses of Ethyl Alcohol. General Chemistry Case studies 5 Pages.*
Wang et al. 1983. Ethanol f rom cellulosic biomass. Philosophical Transactions of Royal Society of London Series B (Phil. Trans. R. Soc. Lond. B), vol. 300, pp. 323-333).*
Freier et al. 1988. Characterization of Clostridium thermocellum JW20. Applied and Environmental Microbiology, vol. 54, No. 1, pp. 204-211.*
Chang et al., Thermophilic, lignocellulolytic bacteria for ethanol production: current state and prespectives, Appln Microbiol Biotechnol, Oct. 2011, 92(1), 13-27.
Taylor et al., Thermophilic ethanologenesis: future prospects for second-generation bioethanol production, Trends Biotechnol, Jul. 2009, 27(7), 398-405.
Sizova et al., Cellulose-and Xylan-Degrading Thermophlic Anaerobic Bacteria from Biocompost, Applied and Environmental Microbiology, Apr. 2011, p. 2282-2291, vol. 77, No. 7.
Shaw et al., Metabolic engineering of a thermophilio bacterium to produce ethanol at high yield, PNAS, Sep. 16, 2008, p. 13769-13774, vol. 105, No. 37.
Mielenz, Biofuels and Biotechnology: Status and Potential, Molecular Biology and Biotechnology, 5th Edition, Ed. J.M. Walker & R. Rapley, Royal Society of Chemistry, 2009, pp. 548-584
Zheng et al., Overview of biomass pretreatment for cellulosic ethanol production, (2009) Int. J. Agric. & Biol. Eng. 2:3, 51-67, Opera Access at http://www.ijabe.org.
Bergquist et al , Molecular diversity of thermophilic cellulolytic and hemicellulolytic bacteria, (1999) FEMS Microbiol. Ecol. 28:99-110.
Lynd et al., Microbial Cellulose Utilization: Fundamentals and Biotechnology, Microbiol. Mol. Biol. Rev., Sep. 2002, p. 506-577, vol. 66, No. 3.
Vanfossen et al., Polysacchride degradation and synthesis by extremely thermophilic anaerobes. Ann. NY Acad. Sci., Mar. 2008, 1125, p. 322-37.
Raman et al., Impact of Pretreated Switchgrass and Biomass Carbohydrates on Clostridium thermocellum ATCC 27405 Cellulosome Composition: A Quantitatve Proteomic Analysis, PLoS ONE, Apr. 2009, e5271, vol. 4, Issue 4.
Zhang et al., Regulation of Cellulase Synthesis in Batch and Continuous Cultures of Clostridium thermocellum, (2005) J. Bacteriol. 187:99-106.
Raman et al., Transcriptomic analysis of Clostridium thermocellum ATCC 27405 cellulose fermentation, BMC Microbiology, 2011, 11:134, http://www.biomedcentral.com/1471-2180/11/134.
Lovitt et al., Ethanol Production by Thermophilic Bacteria: Clostridium thermohydrosulfuricum on Parent and Alcohol-Tolerant Strains of Physiologic Comparison of Solvent Effects, (1984) App Microbiol.48:171-177.
Blumer-Schuette et al., Extremely thermophilic microorganisms for biomass conversion: status and prospects, Curr. Opin. Biotechnol. Jun. 2008, p. 210-217, vol. 19, No. 3.

*Primary Examiner* — Debbie K Ware
*Assistant Examiner* — Kailash C Srivastava
(74) *Attorney, Agent, or Firm* — Scully, Scott, Murphy & Presser, P.C.

(57) ABSTRACT

The present invention is directed to a method of converting biomass to biofuel, and particularly to a consolidated bioprocessing method using a co-culture of thermophilic and extremely thermophilic microorganisms which collectively can ferment the hexose and pentose sugars produced by degradation of cellulose and hemicelluloses at high substrate conversion rates. A culture medium therefor is also provided as well as use of the methods to produce and recover cellulosic ethanol.

8 Claims, 5 Drawing Sheets

(56) References Cited

OTHER PUBLICATIONS

Blumer-Schuette et al., Phylogenetic, Microbiological, and Glycoside Hydrolase Diversities with the Extremely Thermophilic, Plant Biomass-Degrading Genus Caldicellulosiruptor, App. Microbiol., Dec. 2010, p. 8084-8092, vol. 76, No. 24.

Blumer-Schuette et al., Complete genome sequences for the anaerobic, extremely thermophilic plant biomass-degrading bacteria Caldicellulosiruptor hydrothermalis, Caldicellulosiruptor kristjanssonii, Caldicellulosiruptor kronotskyensis, Caldicellulosiruptor owensensis and Caldicellulosiruptor lactoaceticus, J. Bacteriol , Mar. 2011, p. 1483-4; vol. 193, No. 6, pub Mar. 2011; e-published Jan. 7, 2011.

Hamilton-Brehm et al , *Caldicellulosiruptor obsidians* sp. nov., an Anaerobic, Extremely Thermophilic, Cellulolytic Bacterium Isolated from Obsidian Pool, Yellowstone National Park, App. Environ. Microbiol., Feb. 2010, p. 1014-1020, vol. 76, No. 4.

Mielenz et al. (2010) Abstract from "The 32nd Symposium on Biotechnology for Fuel and Chemicals" (Apr. 19-22, 2010).

Zhang et al., Quantification of Cell and Cellulase Mass Concentrations during Anaerobic Cellulose Fermentation: Development of an Enzyme-Linked Immunosorbent Assay-Based Method with Application to Clostridium thermocellum Batch Cultures, Anal. Chem., Jan. 15, 2003, 219-221, 75.

Holwerda et al , A defined growth medium with very low background carbon for culturing Clostridium thermocellum, J. Ind. Microbiol. Biotechnol., e-published Jan. 14, 2012, DOI 10.1007/s10295-012-1091-3.

Ozkan et al., Characterization of 13 newly isolated strains of anaerobic, cellulolytic, thermophilic bacteria, (2001) J. Ind. Microbiol. Biotechnol. 21:275-280.

Kumar el al., Bioconversion of lingocellulosic biomass: biochemical and molecular perspectives, J. Ind. Microbiol Biotechnol., May 2008, p. 377-391, vol. 35, No. 5.

\* cited by examiner

CONSOLIDATED BIOPROCESSING METHOD USING THERMOPHILIC MICROORGANISMS

CROSS REFERENCE TO RELATED APPLICATIONS

The present application claims benefit of U.S. Provisional Application No. 61/596,962, filed on Feb. 9, 2012, the contents of which is incorporated herein by reference.

STATEMENT REGARDING FEDERALLY SPONSORED RESEARCH

This invention was made with government support under DE-AC05-00OR22725 awarded by the U.S. Department of Energy. The government has certain rights in this disclosure.

FIELD OF THE INVENTION

The present invention is directed to a method of converting biomass to biofuel, including a consolidated bioprocessing method, in which a co-culture of two thermophilic microorganisms collectively ferments the hexose and pentose sugars produced by degradation of cellulose and hemicelluloses at high substrate conversion rates.

BACKGROUND OF THE INVENTION

Lignocellulosic biomass represents one of the most abundant renewable resources on Earth. It is formed of three major components—cellulose, hemicellulose, and lignin—and includes, for example, agricultural and forestry residues, municipal solid waste (MSW), fiber resulting from grain operations, waste cellulosic products (e.g., paper and pulp operations), and energy crops. The cellulosic and hemicellulosic polymers of biomass can be hydrolyzed into their component sugars, such as glucose and xylose, which can then be fermented by microorganisms to produce ethanol. Conversion of even a small portion of the available biomass into ethanol could substantially reduce current gasoline consumption and dependence on petroleum.

Multiple conversion processes have evolved for breakdown of biomass to produce bioenergy. These processes vary from multi-enzyme and multi-fermentation approaches called separate hydrolysis and fermentation (SHF) [Wilke et al. (1976) Biotechnol. Bioeng. Symp. 6:55] to simpler simultaneous cellulose hydrolysis (or saccharification) and fermentation (SSF) [Takagi et al. (1977) in Proceedings of the Bioconversion Symposium, Indian Institute of Technology, New Delhi, pp. 55-571; Spindler (1988) Appl. Biochem. Biotechnol. 17:279-294; Alfani (2000) J. Ind. Microbiol. Biotechnol. 25:184-192]. In an SHF process, the cellulosic biomass is hydrolyzed with cellulases to liberate fermentable glucose followed by a separate step for fermentation to ethanol. The SSF process combines the enzymatic hydrolysis and fermentation simultaneously, reducing the process complexity. A natural extension is simultaneous saccharification and cofermentation (SSCF) using microorganisms that are able to convert both hexose and pentose sugars to ethanol. This process simplification culminates with the development of fermentation microorganisms that produces their own enzymes for cellulose hydrolysis, called consolidated bioprocessing (CBP). CBP involves four biologically-mediated events: (1) enzyme production, (2) substrate hydrolysis, (3) hexose fermentation and (4) pentose fermentation. In contrast to conventional approaches, with each step performed independently, all four events may be performed simultaneously in a CBP configuration. This strategy requires a microorganism that utilizes both cellulose and hemicellulose. A CBP process that utilizes more than one organism to accomplish the four biologically-mediated events is referred to as a consolidated bioprocessing co-culture fermentation. Currently there is a lack of a fermentation microorganism that can effectively hydrolyze cellulose and hemicellulose as well as convert all biomass sugars, especially xylose and arabinose as well as glucose, to final products.

An ideal CBP microorganism should be able to produce ethanol as sole product, hydrolyze cellulose to fermentable oligomers, hydrolyze hemicellulose to fermentable oligomers, ferment cellulose oligomers, ferment xylose or xylose oligomers, produce ethanol in high titer (resistant to up to 45% ethanol), be resistant to up to 1% acetic acid from hemicelluloses, grow at thermophilic temperatures ranging from 55 to 80° C., be moderately resistant to common pretreatment inhibitors (furans, polyphenolics) and produce a multi-carbohydrase portfolio on the cellulosome [Mielenz (2009) in *Molecular Biology and Biotechnology*, 5th Edition, Ed. J. M. Walker & R. Rapley, Royal Society of Chemistry, pp: 548-584]. No such single microorganism is presently known and the present invention addresses this need by providing two groups of microorganisms which have together satisfy many of these characteristics, and when co-cultured, can efficiently achieve CBP.

SUMMARY OF THE INVENTION

The present invention relates to a method of converting biomass to biofuel, and particularly to the production of cellulosic ethanol and other fermentation products. This method is efficient and is readily adapted for consolidated bioprocessing. The method comprises co-culturing biomass with a first cellulolytic, thermophilic microorganism and a second hemicellulolytic, extremely thermophilic, xylose-fermenting microorganism for a time and under conditions sufficient to ferment hexose and pentose sugars, produced as said biomass is hydrolyzed and converted to biofuel, with a substrate conversion rate of at least 50%. Substrate conversions of more than 75% can be obtained. In preferred embodiments, the first thermophilic microorganism is a *Clostridium* species, and more preferably, *Clostridium thermocellum*, while the second thermophilic microorganism is a *Caldicellulosiruptor* species, and more preferably, *Caldicellulosiruptor obsidiansis*. The conversion/fermentation process is done at a temperature compatible for both microorganisms, and in some cases at the optimal growth temperature of the first thermophilic microorganism. When the method comprises co-culturing with *C. thermocellum* and *C. obsidiansis*, a preferred growth temperature is 60° C.

In one embodiment, the invention provides a consolidated bioprocessing method of converting biomass to biofuel which comprises co-culturing biomass with an *Clostridium thermocellum* and a *Caldicellulosiruptor* species for a time and under thermophilic conditions sufficient to ferment the hexose and pentose sugars that are produced as the biomass is hydrolyzed and converted to biofuel. In another embodiment, the co-cultured microorganisms are *C. thermocellum* strain ATCC 27405 and said *Caldicellulosiruptor* species is *C. obsidiansis* strain OB47$^T$ (also interchangeably referred to herein as *C. obsidiansis* strain OB47).

Another aspect of the invention is directed to a culture medium which comprises 50% *C. thermocellum* MTC medium blended with 50% *C. obsidiansis* medium lacking sulfide (defined herein as Hamilton-Brehm medium).

Yet another aspect of the invention relates to a method of producing cellulosic ethanol by co-culturing biomass with a first cellulolytic, thermophilic microorganism and a second hemicellulolytic, extremely thermophilic, xylose-fermenting microorganism for a time and under conditions sufficient to achieve a substrate conversion rate of at least 50% and to ferment hexose and pentose sugars, and thereby producing ethanol in the culture; and (b) recovering the ethanol from the culture. Ethanol recovery from a culture can be done by distillation or other techniques known in the art.

DETAILED DESCRIPTION OF THE INVENTION

Figure 1:
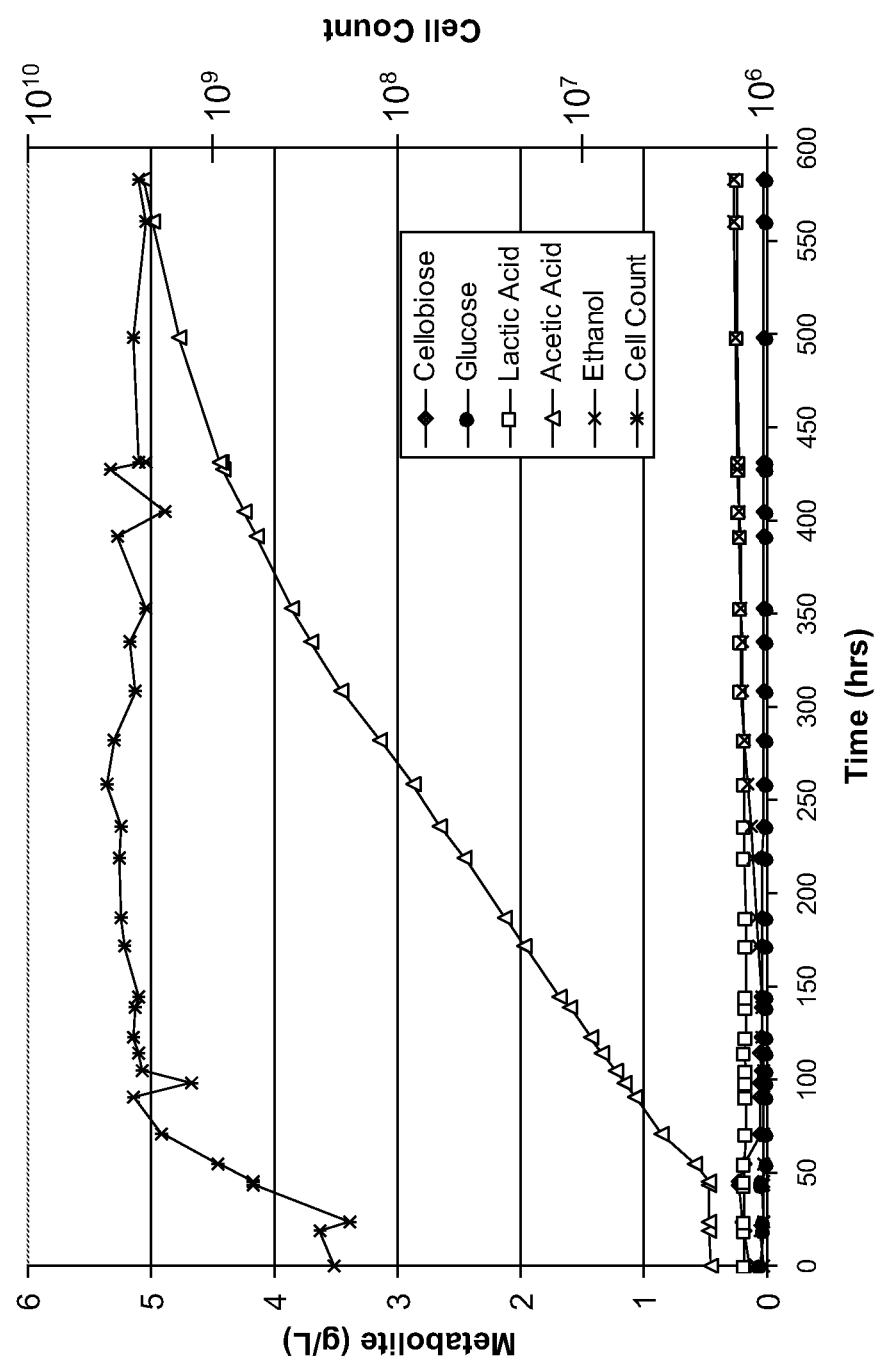
FIG. 1 graphically illustrates fermentation of cellulose by *C. obsidiansis* strain OB47 cultured on 30 g/L cellulose. Cell growth (*) was followed and metabolites were measured as a function of time (h): acetate ($\Delta$); lactate ($\square$); ethanol (x) and cellobiose ($\blacklozenge$).

The present invention relates to a co-culture fermentation process to efficiently convert biomass into biofuel. The invention provides two groups of thermophilic microorganisms that, in a single fermentation can effectively hydrolyze cellulose and hemicellulose and convert the resultant hexose and pentose sugars, including xylose, to ethanol and acetic acid for bioenergy use. The ethanol and acetic acid (or other fermentation by products which can supply energy) from such processes is often referred to as biofuel. However, biofuel is fuel that derives its energy from biological carbon fixation and covers many types of energy sources including ethanol, butanol, biodiesel (produced from biological oils and fats), bioethers, biogas (methane) and even biomass (when used in combustion processes). For purposes of this invention, biofuel is one or more of the energy-yielding molecules produced by the biological hydrolysis and fermentation of biomass. For example, biofuel obtained from biomass can include 2-4 carbon atom alcohols, such as ethanol and (iso) butanol, as well as acetate. Biofuel, as used herein, refers to at least one or more of the products obtained from biomass hydrolysis and fermentation, and thus is not limited to any particular combination of products that are produced, e.g., such as ethanol and acetic acid, singly or in combination. Additionally, ethanol is sometimes referred to as bioethanol, cellulosic ethanol, corn ethanol and other names, usually to reflect the source from which the ethanol is obtained, and all such sources of ethanol are contemplated by the present invention. Ethanol has the chemical formula $CH_3CH_2OH$, no matter its source or production method.

In one embodiment, a method to produce biofuel converts biomass to biofuels by co-culturing biomass with a first cellulolytic, thermophilic microorganism and a second, hemicellulolytic, extremely thermophilic, xylose-fermenting microorganism for a time and under conditions sufficient to ferment the hexose and pentose sugars, which are produced as the biomass is hydrolyzed and converted to biofuel such that fermentation provides a high level of substrate conversion. It has been unexpectedly found that these two classes of microorganisms overcome previous problems of using growth-compatible microorganisms, especially for consolidated bioprocessing. In particular, microorganisms with these characteristics are compatible to hydrolyze and ferment biomass with respect to growth temperature, growth media and, further, without producing growth inhibitory substances.

Biomass is a renewable resource and thus it is advantageous to have a simple method to convert it to biofuel as afforded by the present invention. Biomass has three main structural components—typically, 33-50% cellulose, 17-35% hemicellulose and 12-24% lignin—with the remainder being minerals, protein and other minor materials. Biomass is primarily lignocelluosic plant material but may include non-plant waste materials such as animal waste. Hence, "biomass" as used herein, includes, but is not limited to, forestry residue, agricultural residue, municipal solid waste (MSW), animal waste, yard waste, wood products, fiber resulting from grain operations, waste cellulosic products (e.g., paper and pulp operations), grasses, and energy crops whether grown for biomass production or for other purposes. When used in the present invention, one or more types of biomass can be cultured with the microorganisms of the invention. In other words, the embodiments of the invention can use any type of biomass, alone or in any combination or in any ratio. It is within the ken of the art to select and combine biomass types for use in the present invention. For example, the biomass can comprise an energy crop alone, or municipal solid waste and yard waste, or forestry residue, paper waste and pulp waste, and on in any of the many possible combinations.

In accordance with the invention, biomass can be used with or without pretreatment before co-culturing with the two microorganisms. Pretreatment can be done by physical (e.g., grinding), chemical (e.g., acid treatment) or biological (e.g., enzymatic hydrolysis) techniques, and methods therefore are well known in the art [see, e.g., Zheng et al. (2009) Int. J. Agric. & Biol. Eng. 2:51-67].

The general aspects of co-culturing biomass with microorganisms as well as the equipment and apparatus needed are known to the ordinarily skilled artisan or can be readily determined, whether on the laboratory scale or on an industrial scale. See, Mielenz (2009) for an example of an industrial scale production system. Such general aspects include preparation of the biomass, introduction of the biomass and any other media into a fermentation reactor or vessel using sterile techniques, maintaining cultures and stocks of the microorganisms, timing of inoculation, amounts of an inoculum, the form of the inoculum (e.g., from exponentially growing cultures or from lag-phase cultures and otherwise), time length of the fermentation, removal or purification of the biofuel from the fermentation mixture or mash and more.

With regard to the microorganisms, the first microorganism used in the co-culturing is a cellulolytic, thermophilic microorganism, whereas the second microorganism is hemicellulolytic, extremely thermophilic and xylose-fermenting.

Thermophiles have optimal growth temperatures above 50° C., and typically between about 50-60° C. Extreme thermophiles have optimal growth temperatures above 65° C. and typically between about 70-80° C. Often extreme thermophiles are capable of growing at the temperatures used for thermophilic microorganisms. Xylose-fermenting microorganisms are capable of using xylose as at least one of their energy sources and thus produce enzymes have pentose sugar degradation pathways. In some embodiments, the microorganisms of the invention may also be ethanol tolerant.

Cellulolytic microorganisms are capable of hydrolyzing cellulose. These bacteria produce cellulase which hydrolyzes cellulose to produce glucose. Many examples of cellulolytic, thermophilic microorganisms are known. Hemicellulolytic microorganisms produce xyalanases and are thus capable of hydrolyzing hemicellulose to release pentose sugars, especially xylose, that can then be further fermented. Useful reviews describing cellulolytic, thermophiles and/or hemicellulolytic (extreme) thermophiles include, for example, Bergquist et al. (1999) FEMS Microbiol. Ecol. 28:99-110; Lynd et al. (2002) Microbiol. Mol. Biol. Rev. 66:506-577; Vanfossen et al. (2008) Ann. NY Acad. Sci. 1125:322-37. Some specific microorganisms described and known include, the cellulytic thermophile *Clostridium thermocellum* [Raman et al. (2009) PLoS ONE 4(4): e5271 (2009); Zhang et al. (2005) J. Bacteriol. 187:99-106; Raman et al. (2011) BMC Microbiol. 11:134] and *Clostridium thermohydrosulfuricum* [Lovitt et al. (1984) App. Microbiol. 48:171-177]; as well as the hemicellulolytic extreme thermophiles including various *Caldicellulosiruptor* sps. [Blumer-Schuette et al. (2008) Curr. Opin. Biotechnol. 19:210-217; Blumer-Schuette et al. (2010) App. Microbiol. 76:8084-8092; Blumer-Schuette et al. (2011) J. Bacteriol. 193:1483-4; pub March 2011; e-published Jan. 7, 2011] and more specifically *Caldicellulosiruptor obsidiansis* [Hamilton-Brehm et al. (2010) App. Environ. Microbiol. 76:1014-1020; Mielenz et al. (2010) Abstract from "The 32nd Symposium on Biotechnology for Fuel and Chemicals" (Apr. 19-22, 2010)].

Accordingly, in some embodiments, the first microorganism used in the present invention can be a *Clostridium* species. Examples of useful *Clostridium* sps., *C. thermocellum*, *C. straminisolvens*, and *C. thermocopriae*, with *C. thermocellum* being a preferred organism. In some embodiments, the preferred thermophilic microorganisms are anaerobic microorganisms. Any strains from these species that have the required characteristics can be used, including those that have been genetically engineered (by selection or recombinant engineering) to have the requisite characteristics, for example, ethanol tolerant strains can be developed by selection (e.g., by growth and selection in increasing concentrations of ethanol) or by engineering (e.g., by recombinantly introducing an enzyme that increases ethanol tolerance).

*C. thermocellum* is an established bacterium for hydrolysis of cellulose in the biofuel production process. Its growth temperature range is 45-65° C. and it grows optimally at 60° C. Although *C. thermocellum* is an efficient converter of cellulose, it is a poor converter of hemicellulose. Despite the fact that *C. thermocellum* is one of the fastest growing bacteria that can grow on cellulose and typically produces ethanol and acetic acid with minor levels of lactic acid (plus hydrogen), nonetheless it alone cannot achieve the overall high substrate conversion rates of the invention that are desirable for efficient biofuel production from biomass.

In some embodiments, the second microorganism used in the co-culturing aspect of the invention is a hemicellulolytic, extremely thermophilic, xylose-fermenting microorganism. An example of a second microorganism useful in the instant invention is a *Caldicellulosiruptor* species. *Caldicellulosiruptor* sps. are extremely thermophilic, anaerobic, Gram-positive bacteria capable of hydrolyzing hemicellulose and exhibit optimal growth in the temperature range of 70-80° C. The members of this genus are also capable of cofermentation of pentose and hexose sugars, including xylose. The *Caldicellulosiruptor* sps. suitiable for use in the present invention include *C. bescii*, *C. saccharolyticus*. *C. hydrothermalis*, *C. kristjanssonii*, *C. kronotskyensis*. *C. lactoaceticus*, *C. owensensi*, *C. acetigenus* and *C. obsidiansis*. *C. obsidiansis* is a preferred species.

*Caldicellulosiruptor obsidiansis* (*C. obsidiansis*) is an extreme thermophile isolated from Yellowstone National Park (Hamilton-Brehm 2010). *C. obsidiansis* grows optimally at 78° C. and primarily produces acetic acid and lower levels of ethanol. It readily hydrolyzes hemicellulose and to a slower degree, hydrolyzes cellulose.

While use of any combination of first and second microorganisms is contemplated in the methods of the invention, a preferred embodiment has the first and second microorganisms be a *C. thermocellum* strain and a *C. obsidiansis* strain, respectively, and more preferably be *C. thermocellum* strain ATCC 27405 and *C. obsidiansis* strain OB47$^T$ (ATCC Strain No. BAA-2073), respectively.

The growth media temperature for the co-culture must be compatible for growth and activity of the first and second microorganisms. One challenge is to find a compromise temperature and growth medium to take advantage of rapid cellulose degradation by the thermophile and rapid hemicellulose degradation by the extreme thermophile. In accordance with the invention, a growth temperature at or near the optimum growth temperature of the first, thermophilic microorganism of the invention is generally suitable. Moreover, those of skill in the art can determine a suitable and/or optimal growth temperature for conducting the methods of the invention. For co-culturing *C. thermocellum* and *C. obsidiansis*, a temperature of about 60° C. is preferred.

Often the different microorganisms require different nutrients for optimum growth and produce metabolites that inhibit the growth and activity of the other microorganism when grown in co-culture. For example, *C. obsidiansis* cannot grow on MTC medium [Zhang et al. (2003) Anal. Chem. 75:219-227], but surprisingly was able to grow in co-culture without production of toxic by-products on a media that consisted of 50% *C. thermocellum* MTC medium blended with 50% *C. obsidiansis* medium lacking sulfide ("Hamilton-Brehm medium").

The formulations for MTC and Hamilton-Brehm medium are provided in Table 1.

TABLE 1

Media Composition

| Component | Formula | MTC (g/L) | Hamilton-Brehm medium |
|---|---|---|---|
| Carbon source | | | |
| Avicel (optional) | $[C_6H_{10}O_5]_n$ | 5.0 | 1.5% (wt/vol) |
| Cellobiose | $C_{12}H_{22}O_{11}$ | 5.0 | 0.4% (wt/vol) |
| Yeast extract | | — | 0.02% (wt/vol) |

TABLE 1-continued

Media Composition

| Component | Formula | MTC (g/L) | Hamilton-Brehm medium |
|---|---|---|---|
| Buffers and Chelators | | | |
| 3-(N-morpholino) propanesulfonic acid (MOPS) | $C_7H_{14}NNaO_4S$ | — | 10 mM, pH 6.8 |
| Resazurin | $C_{12}H_6NNaO_4$ | 0.001 | 0.25 mg/ml |
| Dipotassium phosphate | $K_2HPO_4$ | 1.0 | — |
| Phosphate Buffer | — | — | 1 mM |
| Citric acid tripotassium salt | $C_6H_5O_7K_3$ | 2.0 | — |
| Citric acid monohydrate | $C_6H_8O_7 \cdot H_2O$ | 1.25 | — |
| Sodium sulfate | $Na_2SO_4$ | 1.0 | — |
| Sodium bicarbonate | $NaHCO_3$ | 2.5 | 6.0 mM |
| Nitrogen source | | | |
| Ammonium chloride | $NH_4Cl$ | 1.5 | 4.7 mM |
| Urea | $CH_4N_2O$ | 2.0 | — |
| Salts and reducing agent | | | |
| Magnesium chloride hexahydrate | $MgCl_2 \cdot 6H_2O$ | 1 | — |
| Magnesium sulfate | $MgSO_4$ | — | 2.5 mM |
| Calcium chloride dihydrate | $CaCl_2 \cdot 2H_2O$ | 0.2 | 0.7 mM |
| Ferrous chloride tetrahydrate | $FeCl_2 \cdot 4H_2O$ | 0.1 | — |
| Ferrous sulfate heptahydrate | $FeSO_4 \cdot 7H_2O$ | — | — |
| Potassium chloride | KCl | — | 4.5 mM |
| Sodium chloride | NaCl | — | 1.0 mM |
| L-cysteine hydrochloride monohydrate | $C_3H_7NO_2S \cdot HCl \cdot H_2O$ | 1.0 | 2.8 mM |
| Vitamins | | | |
| Pyridoxamine Dihydrochloride | | 0.02 | — |
| PABA | | 0.004 | — |
| D biotin | | 0.002 | — |
| Vitamin B-12 | | 0.002 | — |
| ATCC vitamin supplement | | — | 1x |
| Trace Elements | | | |
| Manganous chloride tetrahydrate | $MnCl_2 \cdot 4H_2O$ | 0.00125 | — |
| Zinc chloride or sulfate | $ZnCl_2$ or $ZnSO_4 \cdot 7H_2O$ | 0.0005 | — |
| Cobalt (II) chloride hexahydrate | $CoCl_2 \cdot 6H_2O$ | 0.000125 | — |
| Nickel(II) chloride hexahydrate | $NiCl_2 \cdot 6H_2O$ | 0.000125 | — |
| Cupric sulfate pentahydrate | $CuSO_4 \cdot 5H_2O$ | 0.000125 | — |
| Boric acid | $H_3BO_3$ | 0.000125 | — |
| Sodium molybdate dihydrate | $Na_2MoO_4 \cdot 2H_2O$ | 0.000125 | — |
| ATCC trace elements | | — | 1x |

The formulation for ATCC Vitamins is based on Wolfe's vitamin solution and contains (mg/L): folic acid, 2.000; pyridoxine hydrochloride, 10.000; riboflavin, 5.000; biotin, 2.000; thiamine, 5.000; nicotinic acid, 5.000; calcium pantothenate, 5.000; vitamin $B_{12}$, 0.100; p-aminobenzoic acid, 5.000; thioctic acid, 5.000; and monopotassium phosphate, 900.0. The formulation for ATCC Trace Elements is based on Wolfe's mineral solution and contains (g/L): EDTA, 0.500; $MgSO_4.H_2O$, 3.000; $MnSO_4.H_2O$, 0.500; NaCl, 1.000; $FeSO_4.7H_2O$, 0.100; $Co(NO_3)_2.6H_2O$, 0.100; $CaCl_2$ (anhydrous), 0.100; $ZnSO_4.7H_2O$, 0.100; $CuSO_4.5H_2O$ 0.010; $AlK(SO_4)_2$ (anhydrous), 0.010; $H_3BO_3$, 0.010; $Na_2MoO_4.2H_2O$. 0.010; $Na_2SeO_3$ (anhydrous), 0.001; $Na_2WO_4.2H_2O$, 0.010; and $NiCl_2.6H_2O$, 0.020.

MTC medium can be prepared, for example, by combining six sterile solutions under a nitrogen atmosphere. Sterilization is accomplished by filter sterilizing preparations with a 0.2-µm-pore-size filter (Pall Corp., Ann Arbor, Mich.) for solution E and by autoclaving solutions A, B, C, D, and F. Solution A contains distilled water, Avicel, and 0.2% resazurin (optional). Solution B, which is concentrated 25-fold relative to the final medium, contains citric acid tripotassium salt, citric acid monohydrate, $NaSO_4$, $KH_2PO_4$, and $Na_2CO_3$. Solution C, which is concentrated 50-fold, contains $NH_4Cl$ and urea. Solution D, which is concentrated 50-fold, contains $MgCl_2.6H_2O$, $CaCl_2.2H_2O$, $FeCl_2.4H_2O$, and L-cysteine hydrochloride monohydrate. Solution E, which is concentrated 50-fold, contains pyridoxamine dihydrochloride, PABA, D-biotin, vitamin $B_{12}$, and thiamine. Solution F, which is concentrated 1,000-fold, contains $MnCl_2.4H_2O$, $CoCl_2.6H_2O$, a zinc salt (Cl or $SO_4$), $CuSO_4.5H_2O$, $H_3BO_3$, $Na_2MoO_4.H_2O$, $NiCl_2.6H_2O$, and citric acid monohydrate. The final amount of each ingredient in 1×MTC is provided in Table 1 [Holwerda et al. (2012) J. Ind. Microbiol. Biotechnol., e-published Jan. 14, 2012; Ozkan et al. (2001) J. Ind. Microbiol. Biotechnol. 27:275-280].

For both MTC and Hamilton-Brehm media, the inclusion of Avicel is optional. For instance, Avicel may not be needed in the presence of biomass. Additionally, other media or additional carbon sources can be used in the methods of the invention. Such media can be determined by those of skill in the art. As indicated, a preferred medium for use with *C. thermocellum* strains and *C. obsidiansis* strains as the first and second microorganisms, respectively, is a 50:50 blend of MTC and Hamilton-Brehm media.

The duration needed for co-culturing the two microorganisms for high substrate conversion lasts for the time needed to yield biofuel and can be determined by those of skill in the art. For example, fermentation to end products should occur in the shortest time possible to allow maximum and efficient conversions of the biomass before exhaustion of the substrate.

For the present invention substrate conversion of more than 75% was observed over a reasonable and industrially useful time, ranging from 40 to 150 hours. Hence, substrate conversion should be at least about 50%, 55%, 60%, 65%, 70% or 75% over a time period of from at least about 30 to about 200 hours or from at least about 50 to about 150 hours. As shown in Example 2, significant consumption of the total biomass sugars occurred within about 150 hrs with both microorganisms stressed at either their top end or well below their respective temperature optimum.

Culture conditions can be anaerobic or aerobic as determined by which microorganisms are used. For *Clostridium* sp. and *Caldicellulosiruptor* sp., anaerobic conditions are needed.

Another embodiment of the invention relates to a culture medium which comprises 50% MTC medium blended with 50% Hamilton-Brehm medium. The ingredients of these two media are described in Table 1. In some embodiments, the culture medium consists essentially of 50% MTC medium blended with 50% Hamilton-Brehm medium with or without Avicel and/or with or without resazurin. Those of skill in the art can readily prepare the culture media of the invention.

A further aspect of the invention is directed at recovering ethanol or other biofuel components produced during the co-culture process. Methods for such recovery and downstream processing are known in the art. For example, ethanol can be recovered by distillation, and using a thermophilic process is an advantage in that regard, especially when working on an industrial scale. Ethanol can be removed from fermentation reactors as it is produced to avoid its toxic effects on microorganisms and methods for such removal are known in the art. Accordingly, the invention provides a method of producing cellulosic ethanol which by co-culturing biomass as described hereinabove and recovering the ethanol.

Further, in other embodiments, the invention provides for efficient, co-hydrolysis of cellulose and hemicellulose and the fermentation of the sugars glucose and xylose to ethanol and acetic acid in a consolidated bioprocessing co-culture format. This method proceeds by co-culturing a first cellulolytic, thermophilic microorganism and a second, hemicellulolytic, extremely thermophilic, xylose-fermenting microorganism with biomass as described herein. Thus, the embodiments of the invention also include a method to produce biofuel that consists essentially of co-culturing a first, cellulolytic, thermophilic microorganism and a second, hemicellulolytic, extremely thermophilic, xylose-fermenting microorganism with biomass for a time and under conditions sufficient to ferment hexose and pentose sugars, produced as said biomass is hydrolyzed and converted to biofuel, with a substrate conversion rate of at least 50%.

All the methods of the invention can be practiced on any scale, from small batches in a laboratory to industrial scale production. See, Mielenz (2009) for an example of an industrial scale production system. One advantage of the present method is that it can reduce the number of fermentation tanks needed and thus provides a significant cost savings other methods. While a preferred way to practice the method of the invention is in a consolidated bioprocessing (CBP) format (technically, a co-culture CBP since two classes of microorganisms are used simultaneously), the method can be practiced with other known bioconversion processes, including SSF and SSCF processes in which additional enzymes for hydrolyzing cellulose or hemicellulose can be added to the fermentation (or can precede fermentation). The preferred growth format is CBP, i.e., without added enzymes.

The foregoing is considered as illustrative of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. All references patents, patent applications or other documents cited are herein incorporated by reference in their entirety.

Example 1

Fermentation of Xylan and Cellulose by *C. Obsidiansis*

*C. obsidiansis* strain OB47 growth and production of metabolites on various ratios of cellulose and hemicellulose was determined on (1) cellulose alone, (2) 2:1 cellulose to hemicellulose and (3) 1:1 cellulose to hemicellulose. The strains were grown on the indicated amounts of cellulose and hemicellulose at 75° C. with an additional ammonium source (5 g/L) and a complex vitamin source (from *C. thermocellum*; Ozkan 2001). For (1), the media contained 30 g/L cellulose; for (2), the media contained 15 g/L cellulose and 7.5 g/L xylan (birchwood or beechwood); and for (3), the media contained 7.5 g/L cellulose and 7.5 g/L xylan. The production of acetate, lactate, ethanol and cellobiose as well as cell density was determined for each condition.

On cellulose alone (FIG. 1), fermentation proceeded slowly and produced acetate as the primary product. Acetate production began in exponential phase and only a small amount of lactic acid was produced. The fermentation was lengthy but showed linear acetate production nearly throughout. Significant amounts of cellulose remained with 90% conversion reached at about 425 hours. Hence, fermentations lasting over three weeks can be expected for *C. obsidiansis*.

Figure 2:
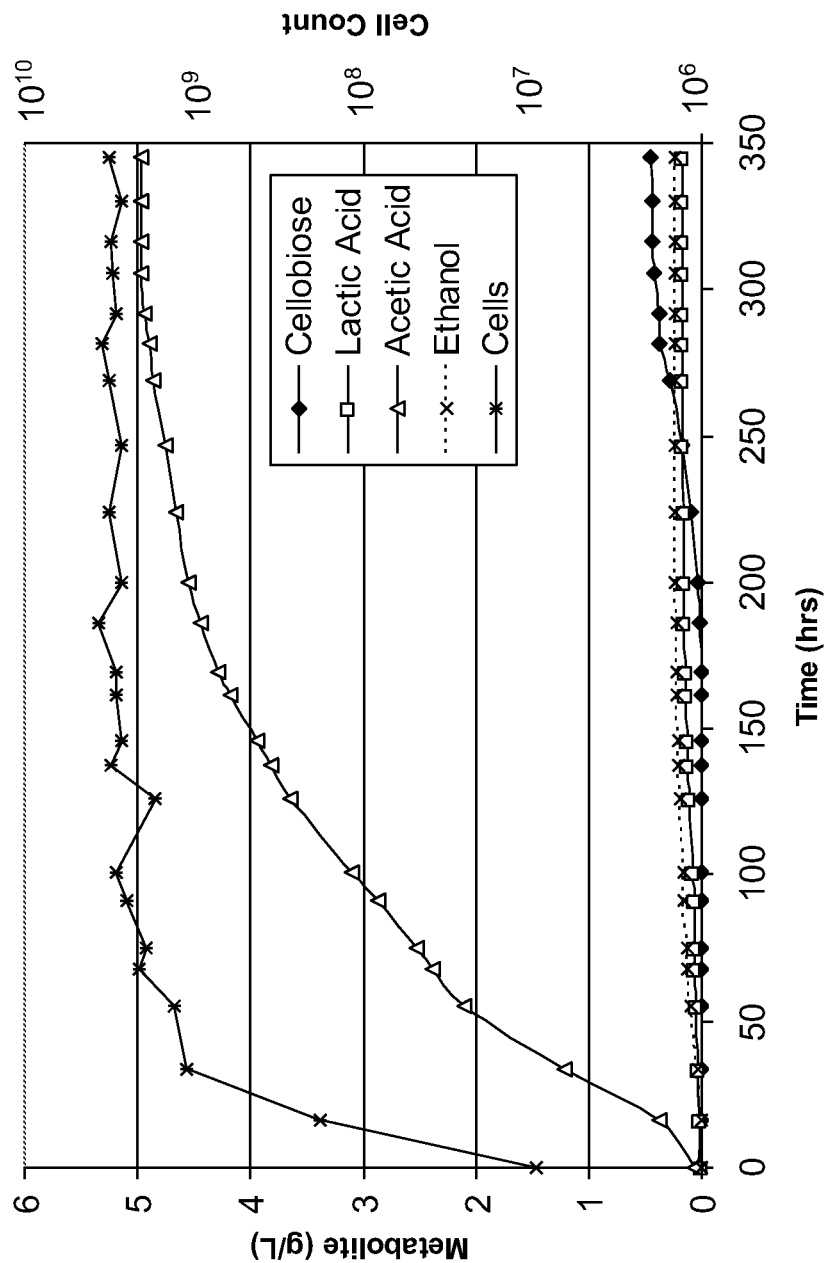
FIG. 2 graphically illustrates fermentation of 2:1 cellulose: hemicellulose by *C. obsidiansis* strain OB47 cultured on 15 g/L cellulose and 7.5 g/L xylan. Cell growth (*) was followed and metabolites were measured as a function of time (h): acetate ($\Delta$); lactate ($\square$); ethanol (---x---) and cellobiose ($\blacklozenge$).
Figure 3:
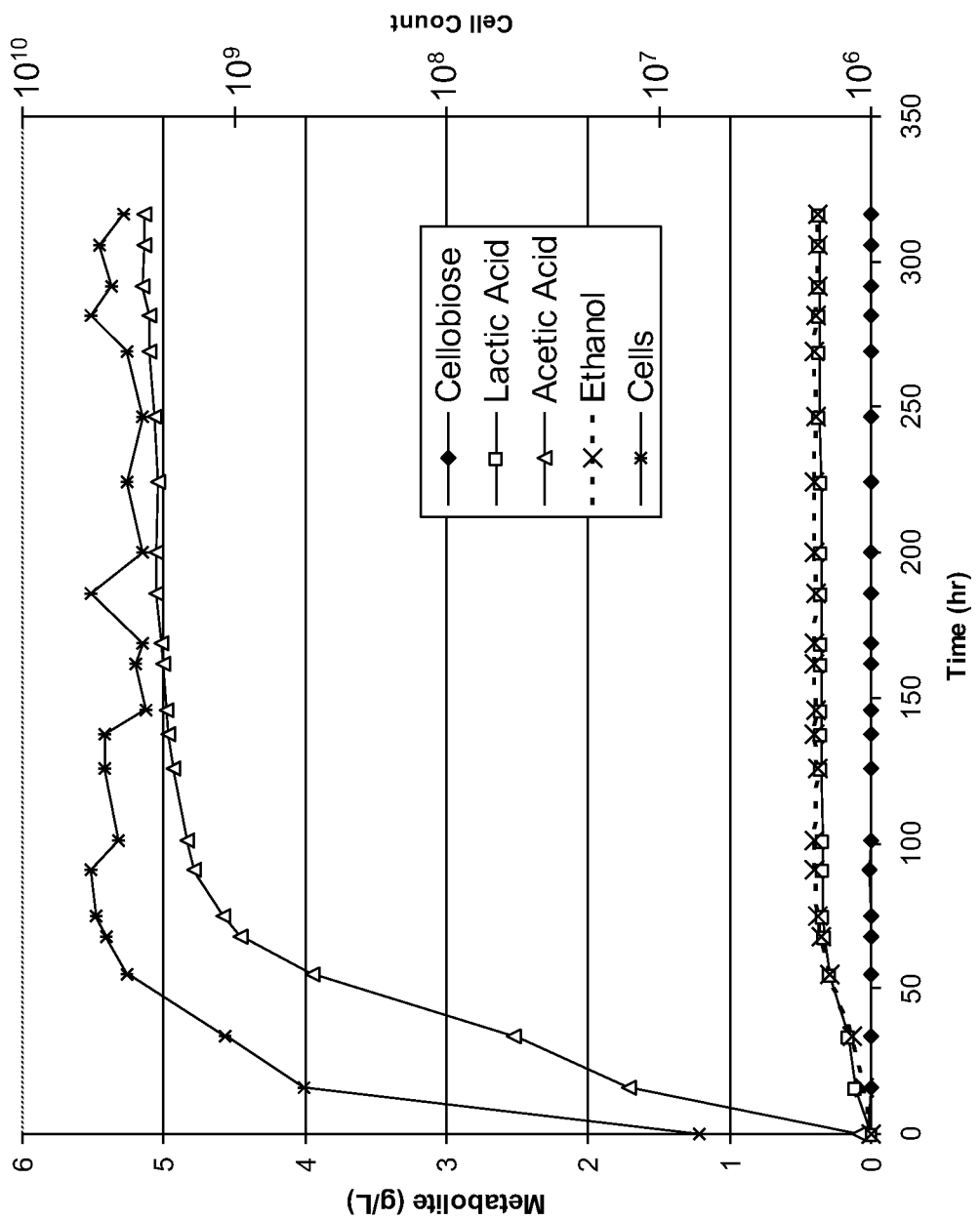
FIG. 3 graphically illustrates fermentation of 1:1 cellulose: hemicellulose by *C. obsidiansis* strain OB47 cultured on 7.5 g/L cellulose and 7.5 g/L xylan. Cell growth (stars) was followed and metabolites were measured as a function of time (h): acetate ($\Delta$); lactate ($\square$); ethanol (---x---) and cellobiose $\blacklozenge$.

On the 2:1 blend (FIG. 2), fermentation proceeded more rapidly and 90% conversion was reached at about 180 hours. On equal amounts of cellulose and hemicellulose (FIG. 3), fermentation was even faster with 90% completion reached at about 60 hours. In all instances, little lactic acid or ethanol were produced. Hence, increased xylan supported faster cell growth and more rapid conversion of substrate to product. Both these fermentations produced more than 5 g/L acetate and cell densities reached about $4\times10^9$ cells/mL. The higher cellulose fermentation slowed at the end liberating free cellobiose.

Figure 4:
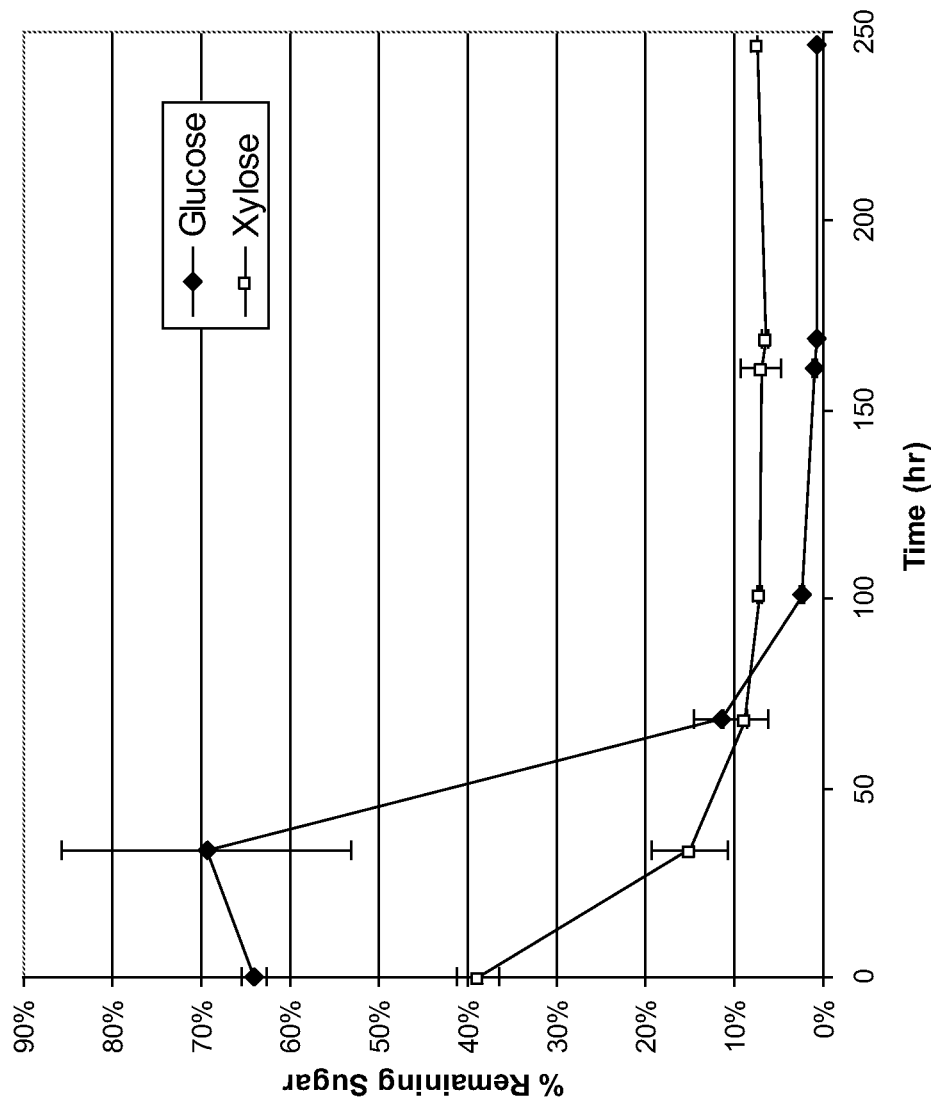
FIG. 4 graphically illustrates residual glucose ($\blacklozenge$) and xylose ($\square$) as a function of time (h) for culture shown in FIG. 3.

The 1:1 cellulose:hemicellulose fermentation was analyzed for total carbohydrates using a quantitative saccharification assay to determine residual glucose and xylose, confirming that 90% of substrate was consumed in about 60 hours (FIG. 4). The overabundance of glucose at time zero is from the presence of some cellulose in commercial xylan. Cellulose (as glucose) was essentially completely consumed while residual xylan (as xylose) remained at the end of the fermentation. OB47 did not demonstrate the typical diauxic lag for xylose consumption.

Overall, *C. obsidiansis* preferentially consumes hemicellulose and the presence of hemicellulose facilitates cellulose conversion.

Example 2

Biomass Cofermentation with *C. Thermocellum* and *C. Obsidiansis*

A mixture of 5 g/L pretreated switchgrass (NREL) and 7.5 g/L birchwood xylan was fermented with a mixed culture of C. thermocellum strain 27405 and C. obsidiansis strain OB47 using a 50-50 blend of MTC medium (Zhang 2003) and OB47 medium without sulfide (Hamilton-Brehm 2010). C. obsidiansis cannot grow in MTC medium. The starting carbohydrate composition was 4.2 g/L FR xylose, and 2.6 g/L FR glucose (as cellulose) with the remainder of the weight as other sugars, lignin, ash and other unidentified substituents. Fermentation was conducted at 60° C. Due to the thick fermentation broth, cell mass was not followed and visually the two microorganisms cannot be distinguished in culture. (FR refers to fermentation residues or remaining cellulose or hemicellulose).

Figure 5:
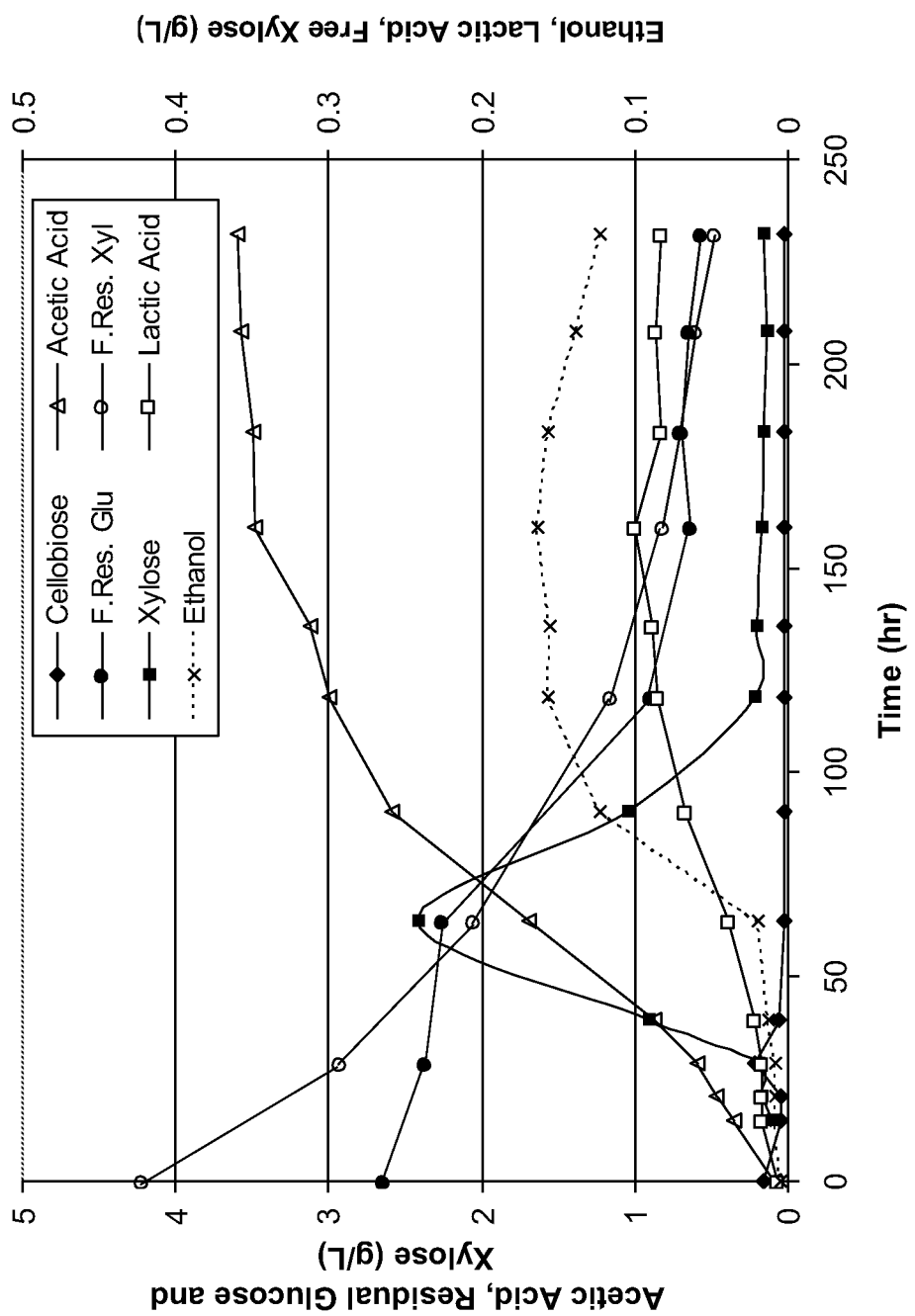
FIG. 5 graphically illustrates cofermentation of cellulose and hemicellulose with a mixed culture of *C. thermocellum* strain 27405 and *C. obsidiansis* strain OB47 cultured on 5 g/L pretreated switch grass and 7.5 g/L xylan. Metabolites were measured as a function of time (h): acetate (-$\Delta$-); lactate (-$\square$-); ethanol (---x---), fermentation glucose (-$\bullet$-), fermentation xylose (-o-) and free xylose (-$\blacksquare$-).

FIG. 5 evidences that both microbes contribute to the fermentation. First, xylose hydrolysis and consumption was immediate with a small amount of free xylose building up until C. obsidiansis fermentation caught up. Since C. thermocellum cannot use xylose, the xylose is being consumed by C. obsidiansis. Significant cellulose consumption did not start until about 60 hours at which time ethanol and lactic acid accumulation began, suggesting that C. thermocellum metabolism was responsible, especially since C. obsidiansis fermentations conducted as in Example 1 generated little ethanol and lactic acid. (It is noted that C. obsidiansis can generate ethanol only under different fermentation conditions not relevant to the conversion of biomass to biofuel.) Assuming a 2:1 acetate to ethanol ratio, suggests that C. thermocellum contributed up to 10% of the acetic acid, and all the ethanol and lactic acid. The use of about 78% of the cellulose and 89% of the xylan in a mixed substrate including switchgrass in about 150 hours is a significant accomplishment given the potential for inhibitory compounds. The mixed culture achieved both rapid cellulose and hemicellulose hydrolysis.

Accordingly, C obsidiansis can ferment biomass substrates well below its temperature optimum permitting it to be paired with strong cellulose hydrolyzing partner microbes like C. thermocellum.

What is claimed is:

1. A method of converting biomass to biofuel which comprises co-culturing in a fermentation reactor biomass with a first cellulolytic, thermophilic microorganism and a second hemicellulolytic, extremely thermophilic, xylose-fermenting microorganism for a time and under conditions sufficient to ferment hexose and pentose sugars which are produced as said biomass is hydrolyzed and converted to biofuel and to ferment said sugars at a substrate conversion rate of at least 50% over a period of about 50 to about 150 hours, wherein said first microorganism is *Clostridium thermocellum* and said second microorganism is *Caldicellulosiruptor obsidiansis* and said co-culturing is conducted at 60° C.

2. The method of claim 1, wherein said *Clostridium* species is *C. thermocellum* strain ATCC 27405 and said *Caldicellulosiruptor* species is *C. obsidiansis* strain OB47$^T$ (ATCC BAA-2073).

3. The method of claim 1, wherein biofuel comprises ethanol and/or acetate.

4. The method of claim 1, wherein said pentose sugar is xylose.

5. A method of producing cellulosic ethanol which comprises:
   (a) co-culturing in a fermentation reactor biomass with a first cellulolytic, thermophilic microorganism and a second hemicellulolytic, extremely thermophilic, xylose-fermenting microorganism for a time and under conditions sufficient to ferment hexose and pentose sugars to produce ethanol at a substrate conversion rate of at least 50% over a period of about 50 to about 150 hours, wherein said first microorganism is *Clostridium thermocellum* and said second microorganism is *Caldicellulosiruptor obsidiansis* and said co-culturing is conducted at 60° C.; and
   (b) recovering said ethanol.

6. The method of claim 5, wherein said ethanol is recovered by distillation.

7. The method of claim 5, wherein said substrate conversion rate is at least 75%.

8. The method of claim 5, wherein said *Clostridium* species is *C. thermocellum* strain ATCC 27405 and said *Caldicellulosiruptor* species is *C. obsidiansis* strain OB47$^T$ (ATCC BAA-2073).

* * * * *